United States Patent [19]

Smith et al.

[11] Patent Number: 4,988,302
[45] Date of Patent: Jan. 29, 1991

[54] CULTURE MEDIA PACKAGE

[75] Inventors: Jerry W. Smith; Nadine M. Sullivan, both of Ann Arbor, Mich.

[73] Assignee: Difco Laboratories Incorporated, Detroit, Mich.

[21] Appl. No.: 363,505

[22] Filed: Jun. 8, 1989

[51] Int. Cl.⁵ .............................................. C12M 1/22
[52] U.S. Cl. .................................. 435/298; 435/299; 435/296
[58] Field of Search ............... 435/298, 294, 297, 296, 435/292, 285

[56] References Cited

U.S. PATENT DOCUMENTS

| | | | |
|---|---|---|---|
| 4,296,205 | 10/1981 | Verma | 435/285 |
| 4,534,154 | 8/1985 | Gaubert | 383/66 |
| 4,603,105 | 7/1986 | Kaplan | 435/291 |
| 4,634,676 | 1/1987 | Sapatino | 435/294 |
| 4,797,309 | 1/1989 | Krammerer et al. | 206/620 |

Primary Examiner—Larry Jones
Attorney, Agent, or Firm—Barnes, Kisselle, Raisch, Choate, Whittemore & Hulbert

[57] ABSTRACT

A culture media package comprising a container having a bottom wall and a peripheral side wall which is substantially filled with a culture medium, a removable insert over the top wall and having a portion defining a planar undersurface and a removable protective cover over the container and insert. The container and insert have radially extending flanges which are bonded to one another. The package is made by filling the container with a molten culture medium in a sterile environment, bonding the insert to the container in a sterile environment, inverting the sealed container such that the molten medium contacts the planar surface of the insert permitting any gases and bubbles to rise toward a space adjacent the bottom of the container and maintaining the container with the insert thereon in an inverted position until the medium has solidified. The removable cover may be applied to the sealed package of the container and insert either before the sealed package is inverted or after the medium has solidified. The package is preferably made from continuous molded plastic strips of connected containers and connected inserts which are filled with medium and sealed, severed from one another, thereafter inverted while the culture medium is still molten and permitted to remain in the inverted position until the culture medium has solidified.

34 Claims, 8 Drawing Sheets

CULTURE MEDIA PACKAGE

This invention relates to culture media containers and packages.

BACKGROUND AND SUMMARY OF THE INVENTION

It is old and well known to utilize culture media in a container for conducting growth and biochemical reactions wherein the sample of the specimen to be tested is applied to the surface of the medium in the container. Such devices are commonly known as Petri dishes.

Commonly used Petri dishes in the form of a dish having a bottom wall and a peripheral side wall are filled with the molten culture medium and the culture is permitted to solidify or gel. A cover is then loosely applied. In order to prevent surface phenomenon problems such as syneresis, contamination, and condensation of moisture, it has been essential to refrigerate such Petri dishes until they are to be used. Syneresis occurs because of evaporation of the solidified culture medium and the inability of the expelled water vapor to rehydrate the solidified gel. When the temperature differential between the inside of the dish and the environment differ, the effects of this evaporation on the inside cover results in heavy condensation and necessitates that a technician must first dry the interior of the plate before using it. Dehydration occurs more rapidly with warmer temperatures and dry conditions in the environment. Contamination occurs because the cover is loosely applied allowing entrance and exchange of external nonsterile atmospheres.

In an effort to obviate the sterility and dehydration problems, it has been common to provide a plurality of such Petri dishes in a sterile plastic sealed bag. However, it has still been essential to refrigerate the package for certain types of culture media to retard syneresis, contamination and dehydration. Refrigeration has also been necessary for culture media which are subject to oxidation such as those that contain blood, vitamins or antibiotics. Further, refrigeration may be required for extended storage greater than a week. In any event, the shelf life of such culture dishes is very limited, on the order of three or four months. Accordingly, it has been necessary to date the package. As a result, if the package is not used within the time indicated it must be destroyed.

U.S. Pat. No. 4,775,628 proposes to seal a modified Petri dish with a pervious sheet, thereafter apply the molten media through an opening in the bottom wall of the dish, seal the opening and thereafter utilize such a dish in testing by applying the specimen to the pervious sheet. Such an arrangement is not only complex, slow and costly, but necessitates the utilization of a method of using the culture media that has not heretofore been used.

Among the objectives of the present invention are to provide a culture media package which has long shelf life; which minimizes the problems of syneresis, desiccation, and contamination; which provides a smooth surface on the culture medium for receiving the test specimen; which does not require refrigeration; which can be readily shipped; which is not fragile or brittle; which can be provided in various configurations depending upon the type of test needed; which can be utilized in a conventional manner as well known in the art of using Petri dishes; which in some forms provide a Rodac device; which in some forms provide a combined Rodac and conventional culture media package; which is low in cost; which can be produced at high speeds; and which is pleasing in appearance.

In accordance with the invention, the culture media package comprising a container having a bottom wall and a peripheral side wall, a removable insert over the top wall and having a portion defining a planar undersurface bonded to the container and a removable protective cover over said container and insert. The container and insert having radially extending flanges which are bonded to one another. The packages are made by filling the container with molten culture medium in a sterile environment, bonding the insert to the container in a sterile environment, inverting the sealed container such that the molten medium contacts the planar surface of the insert permitting any gases and bubbles to rise toward a space adjacent the bottom of the container and maintaining the container with the insert thereon in an inverted position until the culture medium has solidified. The surface of the culture medium which is to be used for testing takes on the shape of the insert providing the desired test surface when the insert is removed. The removable cover may be applied to the sealed package of the container and insert either before the sealed package is inverted or after the medium has solidified. The package is preferably made from continuous molded plastic strips of connected containers and connected inserts which are filled with medium and sealed, severed from one another, thereafter inverted while the culture medium is still molten and permitted to remain in the inverted position until the culture medium has solidified.

DESCRIPTION

Referring to FIGS. 1-6, the culture media package embodying the invention comprises a plastic container or dish 30 that has a base wall 31 and a peripheral wall 32 which, preferably tapers upwardly and outwardly from said base wall 31. The container 30 also includes a transverse wall or flange 33 that extends radially outwardly from the upper free and open end of the wall 32. The base wall 31 of the container 30 is flat and includes a peripheral portion 34 which is U-shaped in cross section and defines an annular peripheral groove 35.

The package also includes an imperforate plastic insert 36 which includes a first planar portion 37 adapted to extend into the open end of the container 30 and define a planar surface 38. Insert 36 further includes a peripheral wall 39 that extends upwardly and outwardly to a peripheral flange 40 that extends radially from the upper edge of the wall 39. The angle which the peripheral wall 39 makes with a vertical axis is greater than the angle which the peripheral wall 32 of the container 30 makes with a peripheral axis to facilitate insertion of the insert 36 in overlying relationship to the flange 33. Alternatively, the walls 39, 32 may have the same angle, which would require pressure fit of the insert 36 in the container 30. The peripheral flange 40 is sealed to the flange 33.

Figure 5:
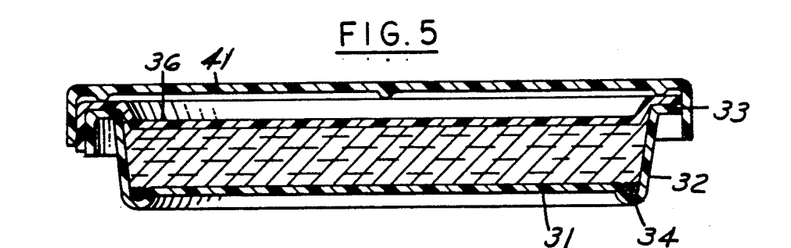
FIG. 5 is a vertical sectional view of the assembled and filled package.

Substantially the entire volume of the package is filled with culture media so that the upper surface of the culture media defines a shape that conforms with the surface 38 of the insert 36. When the insert 36 is removed, the resultant surface on the culture medium is planar for testing. Because of the method of making the package, as presently described, any gases or bubbles that may remain as a result of incomplete filling in the culture medium collect in the space adjacent the bottom defined by groove 35, which is remote from surface 38 and at the junction of the base wall 31 and peripheral wall 32 (FIG. 5).

Figure 1:
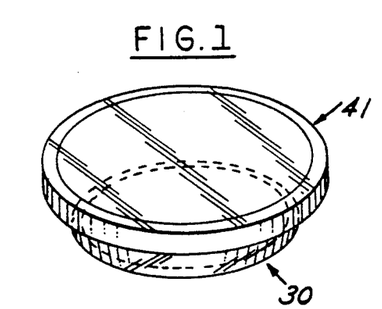
FIG. 1 is a perspective view of a culture medium package embodying the invention.
Figure 4:
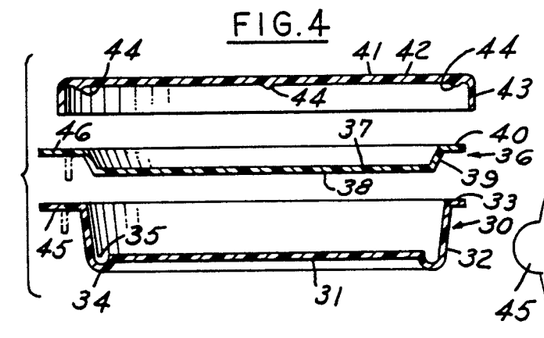
FIG. 4 is an exploded sectional view of the culture medium package.

The package further includes a cover 41 that has a base wall 42 and a peripheral cylindrical downwardly extending wall 43 which is adapted to telescope over the container and insert in loose non-sealing relation thereto. The cover 41 includes circumferentially spaced downwardly extending projections 44 that are adapted to engage the flange 33 after the insert 36 is removed and a test or other procedure is provided. This holds the cover in spaced relation to the container so that the atmosphere of the interior is the same as the exterior, as may be required for incubation.

Figure 2:
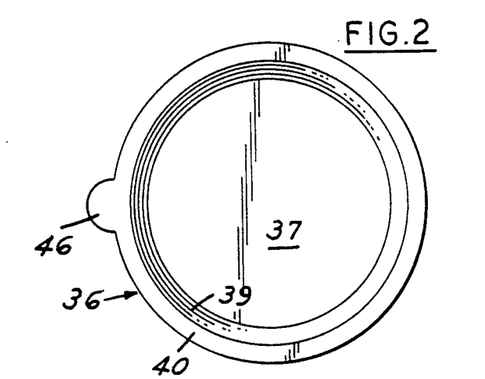
FIG. 2 is a top plan view of the package with the cover removed.
Figure 3:
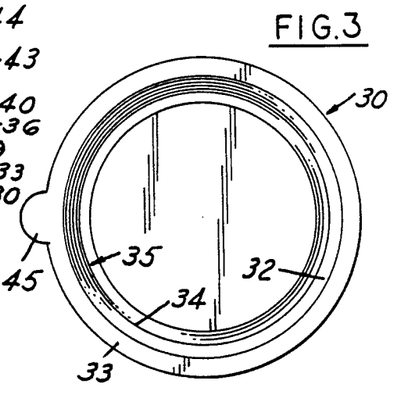
FIG. 3 is a bottom plan view of the package with the cover removed.

Referring to FIGS. 2-4, the container 30 includes a tab 45 extending radially from the flange 33 and the insert 36 includes a tab 46 in overlying relationship to the tab 45 but not sealed or bonded thereto. The tab 45 is connected to the flange 33 by weakened line 47 such as a groove so that it can be flexed downwardly when the cover 41 is provided over the assembled insert and container.

In the manufacture, as presently described, the container 30 is made of relatively rigid plastic material while the insert 36 is made of less rigid flexible but form retaining material. The cover 41 is made of relatively rigid plastic material. The container 30, insert 36 and cover 41 are preferably transparent.

Figure 37:
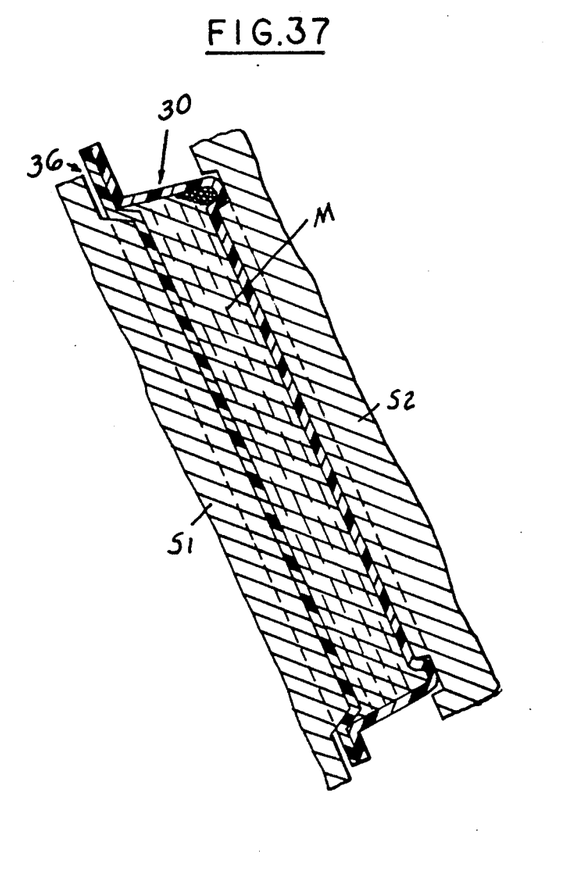
FIG. 37 is a vertical sectional view showing the solidification of the package of the type shown in FIG. 1.

In the manufacture of the package, the container 30 is first filled with a molten culture medium and the insert 36 is brought into position and bonded at the flanges 40, 33. The package is then inverted and the molten medium is permitted to solidify so that the test surface or the culture medium conform with the planar surface 38. By such a method, the culture medium solidifies in situ in conformity with the underside of the surface 38. During the solidification, any gases or bubbles migrate to the space defined by the groove. It is important that the culture medium remain in contact with the surface 38 at all times during solidification. Although the package is preferably inverted 180°, it can be at any angle provided that the culture medium remains in contact with surface 38. As shown in FIG. 37, the culture media package can be inverted 90° and provided between cooled members $S_1$, $S_2$ that have configurations that conform to the insert 36 and bottom 30 to hold the package until the culture media has solidified. In this form, any gases and bubbles collected at the area of juncture of the side wall 32 and groove 34. In both arrangements, substantially the entire surface of the culture package which is to be used for conducting growth and biochemical reactions is planar.

The groove 35 not only defines an integral space adjacent the base wall 31 for gases and bubbles but also provides a rib that increases the rigidity to the container 30 and facilitates adherence of the medium to the container. The groove 35 also forms a rib that facilitates stacking of the packages. Thereafter the package is inverted and the cover 41 is applied. Alternatively, the cover is applied before inverting. During the application of the cover, the tabs 45, 46 flex downwardly within the confines of the peripheral wall 43 of the cover 41.

Figure 6:
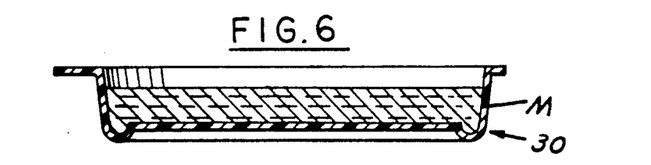
FIG. 6 is a plan view of the container portion of the package.
Figure 7:
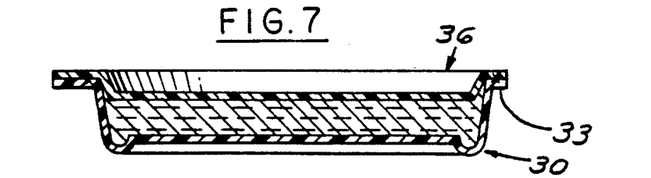
FIGS. 7–11 are sectional views showing the steps in the manufacture and use of the package.
Figure 8:
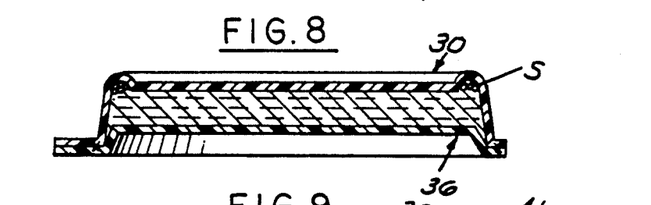
Figure 9:
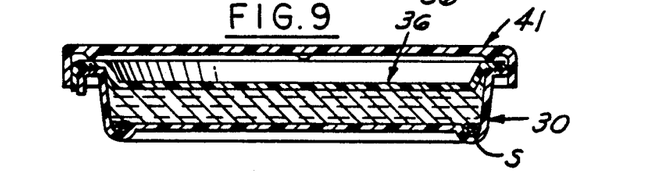
Figure 10:
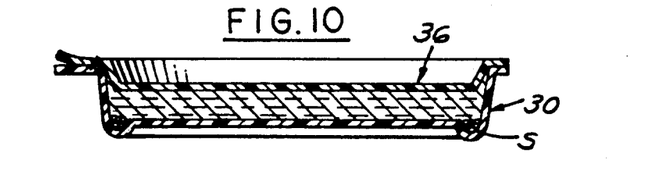

The method of filling and attaching of the insert 36 to the container 30 is more readily understood by reference to FIGS. 6-11. As shown in FIG. 6, the molten medium M is introduced into the sterile container 30 in a sterile environment. The sterile insert 36 is then applied and heat bonded about its entire periphery as at X to the container 30 (FIG. 7). The container 30 and insert 36, now forming a single unit, are inverted (FIG. 8) such that the molten medium is in intimate contact with the surface 38 of the insert 36 and any gas or bubbles entrained in the culture medium migrate to the annular space S defined by groove 35 in the base of the container 30. After the media has solidified, the package is inverted (FIG. 10) and a cover 42 may be applied for storage and shipment.

More specifically, the container 30 and insert 36 are sterile condition before use and the filling of the container is conducted in a sterile atmosphere. After the filling, the space above the container is evacuated and flushed with an inert gas and the sealing by heat is conducted in a controlled atmosphere.

In a preferred method, the forming of the containers and inserts is conducted simultaneously and in a continuous method with the steps of filling, sealing, inverting or flipping over and applying the cover. This is shown schematically in the block diagram of FIG. 3.

Figure 25:
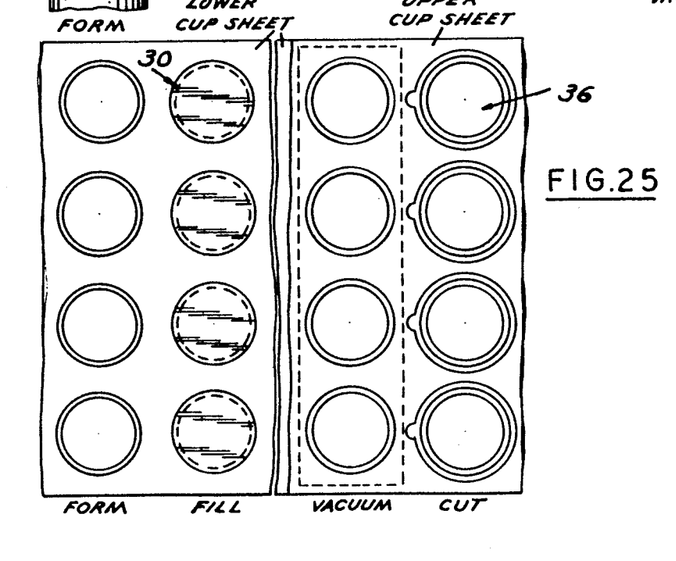
FIG. 25 is a fragmentary schematic plan view of a portion of the system shown in FIG. 23.

In such a method, the plastic material for the inserts and container comprises irradiated roll plastic stock which is kept in sealed plastic bags and in a sterile room until used. The entire method is performed in a controlled sterile atmosphere to prevent contamination. The web for the inserts is successively formed as by thermo-forming and the web for the containers is similar formed as by thermo-forming. The two webs with the formed inserts 36 and containers 30 are then brought together adjacent a filling device F which provides a predetermined quantity molten medium to the container. The webs are then further brought toward one another until the inserts are successively brought into engagement and sealed. This is preferably done in a vacuum and purging environment. The cutting of the filled combined package of insert and container from the web is then performed, the package is inverted onto a horizontal surface and maintained in such position until the culture medium has solidified whereupon the package may be reinverted and the cover applied. The surface may be cooled to accelerate the solidification. As shown in FIG. 25, it is preferable that a plurality of inserts and containers be provided transversely on the webs for maximum efficiency.

In a preferred arrangement, the packages with the covers thereon are stacked to form an array and placed in a bag which is closed and thereby forms a convenient method of handling the culture medium packages much in the manner of present Petri dishes. However, the bag need not be purged or sealed in a hermetic fashion.

Alternatively, as previously indicated, the inserts and containers may be made separately and assembled selectively. Alternatively, the various components including the insert, container and cover can be made by injection molding. Preferably the cover is injection molded even though the insert and container are made by thermo-forming.

Figure 12:
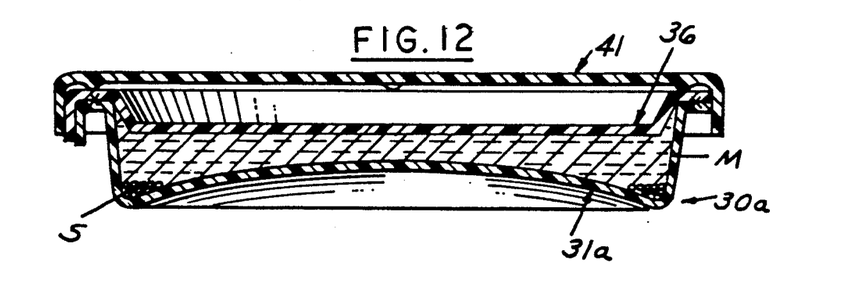
FIG. 12 is a sectional view of a modified package embodying the invention.

In the modified form shown in FIG. 12, the container has a base wall 31a which is concave upwardly to resist the vacuum force during evacuation, purging and sealing especially when the container is made by thermo-forming.

Figure 13:
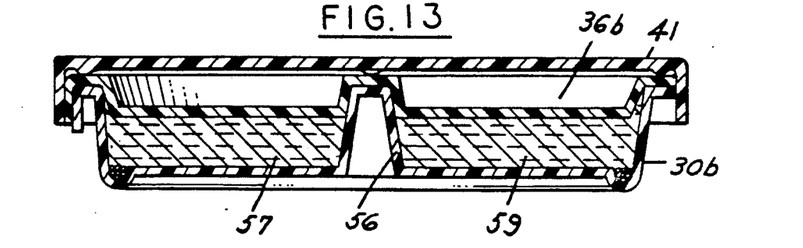
FIG. 13 is a vertical sectional view of a modified form of package.
Figure 14:
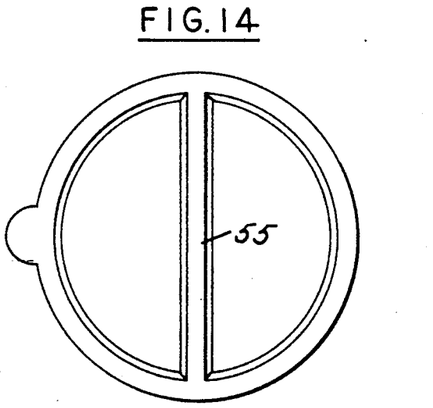
FIG. 14 is a plan view taken of the package shown in FIG. 13 with the cover removed.
Figure 15:
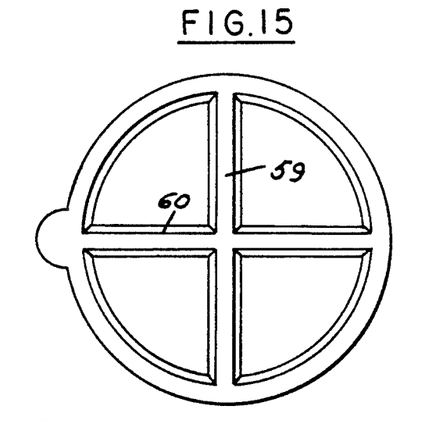
FIG. 15 is a plan view of a further modified form of package with the cover removed.

In the form of package shown in FIGS. 13 and 14, the insert 36b and container 30b are provided with complementary ribs 55, 56 dividing the space for the culture medium into chambers 57, 58. In such a structure, different culture media can be provided in the chambers as may be required for special test. In the form shown in FIG. 15, ribs 59, 60 are provided dividing the culture medium area into four isolated areas.

Figure 16:
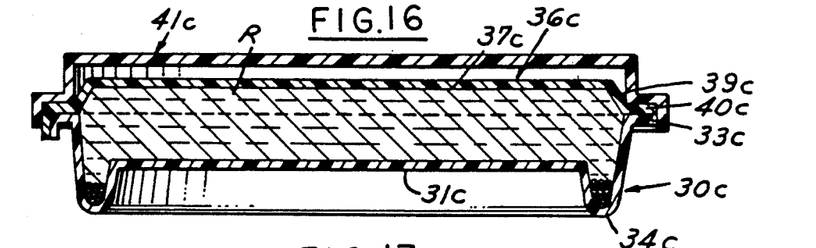
FIG. 16 is a vertical sectional view of another modified form of Rodac type package.
Figure 17:
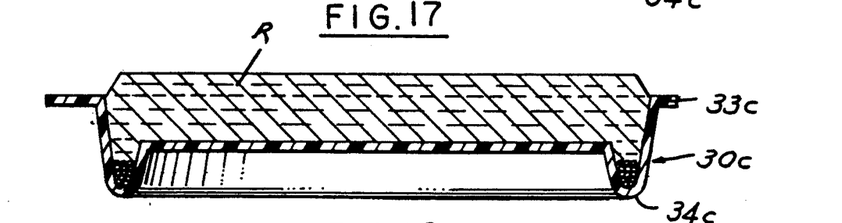
FIG. 17 is a view of the package shown in FIG. 16 with the cover and insert removed.
Figure 18:
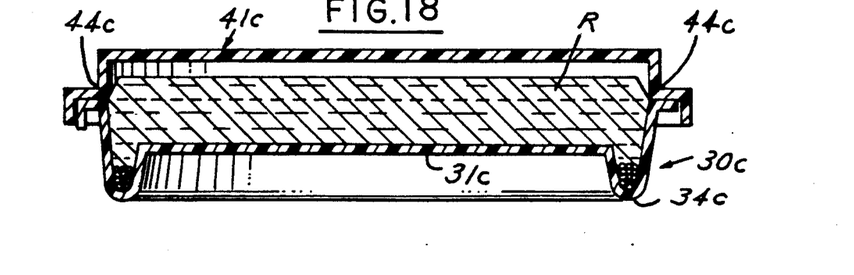
FIG. 18 is a view similar to FIG. 17 showing the cover reapplied.

The form of package shown in FIGS. 16-18 is intended for Rodac procedures wherein it is necessary that the culture medium provide a planar surface projecting upwardly from the periphery of the culture medium mass. In this form, the container 30b has a base wall 31c that is spaced upwardly from the groove 34c. The insert 36c is provided with a base wall 37c that is connected to the flange 40c by a downwardly and outwardly extending wall 39c. As a result when the molten culture medium is provided and the insert 36c sealed to the container 30c and the container is inverted, the culture medium fills the space R so that when the culture medium solidifies the portion of the medium in that space projects upwardly above the plane of the peripheral flange 33c (FIG. 17). When a test is being conducted, the cover 41c can be reapplied as shown in FIG. 18 but in this instance the circumferentially spaced ribs 44c have a greater axial dimension so that they will hold the base 44c of the cover in spaced relation to the upper surface of the culture medium.

Figure 11:
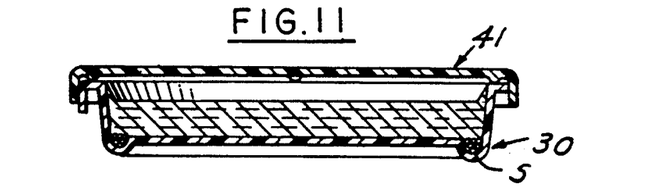

When it is desired to utilize the package, the cover is removed and exposes the planar surface of the medium which up to that time has been preserved in a non-gaseous and sterile condition at its upper surface. As shown in FIG. 11, the cover can be utilized after the insert 36 is removed and while the test is being conducted.

Figure 26:
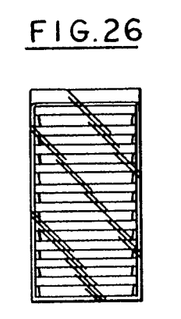
FIG. 26 is a view of a method of placement of a plurality of culture media packages is a bag.

As shown in FIG. 26, a plurality of culture media packages can be stacked and placed in a transparent bag B and sealed at S to provide convenient handling.

Figure 19:
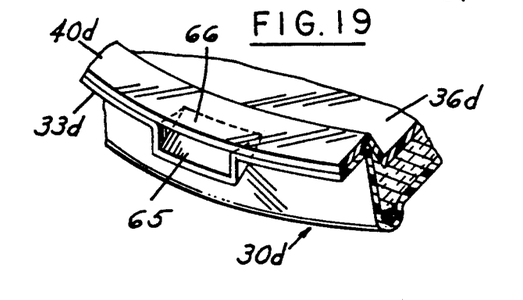
FIG. 19 is a fragmentary perspective view of a modified form of package.

In the modified form shown in FIG. 19, a portion 65 of the peripheral flange 33d of the container 30d is spaced from the peripheral flange 40d as at 65 to provide a tab 66 for grasping the insert 36d for removal. Portions 65, 66 are thus in over line out spaced relation.

Figures 20, 21, 22:
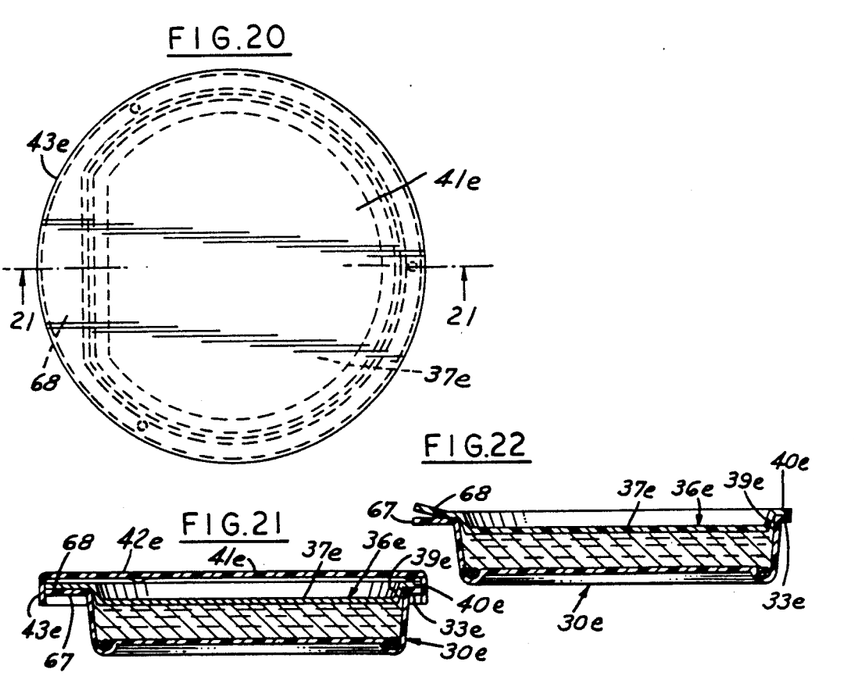
FIG. 20 is a plan view of another modified form of package.
FIG. 21 is a sectional view taken along the line 21—21 in FIG. 20.
FIG. 22 is a fragmentary sectional view of the package shown in FIGS. 20 and 21 with the cover removed and showing the package in process of removal of the insert.
Figure 23:
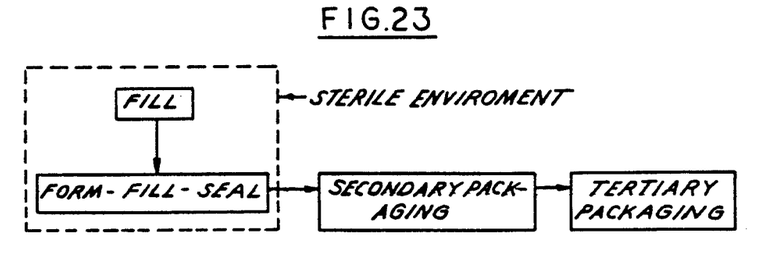
FIG. 23 is a schematic of the method of manufacture of the culture media package.
Figure 24:
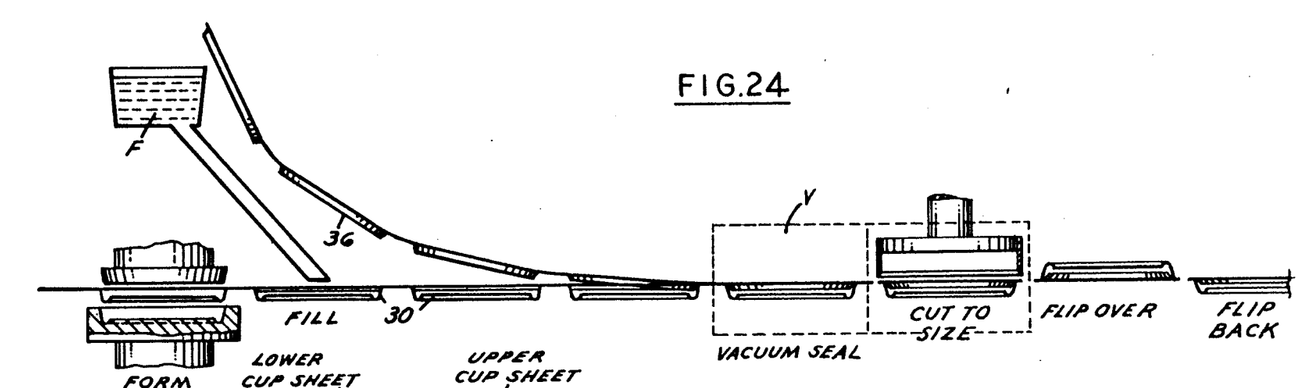
FIG. 24 is a schematic of the overall system of making the package.

In the form of the invention shown in FIGS. 20-22, the cross sectional shape of the container 30e is non-circular herein shown as D-shaped. The bottom wall 37e and peripheral wall 39e of insert 36e have a complementary shape. The flanges 33e and 40e are sealed to one another in a corresponding D-shaped configuration shown as X. However, the flanges 33e and 40e include portion 67, 68 that extend radially outwardly beyond the sealed portions and the free edges of the flanges define a circle. The cover 41e has a base wall 42e that is circular and has a cylindrical peripheral wall 43 that telescopes over the flanges. Thus the overall appearance of the package is generally cylindrical. At the same time the overlapping portion 67, 68 are not sealed to one another so that the flexible tab 68 of the insert can be used to remove the insert 36e.

Figure 29:
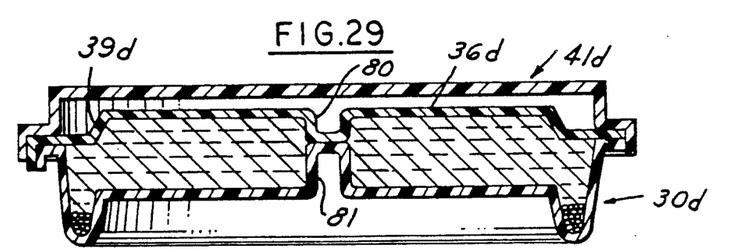
FIG. 29 is a vertical sectional view through a further modified form of Rodac type culture media package.
Figure 30:
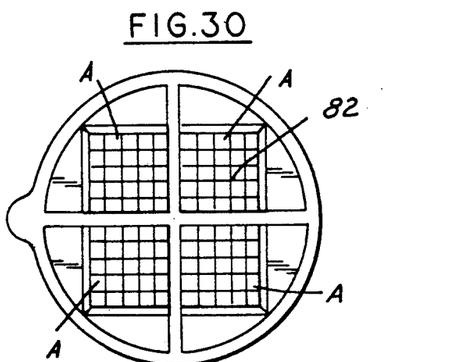
FIG. 30 is a plan view of the package with the cover and insert removed.
Figure 31:
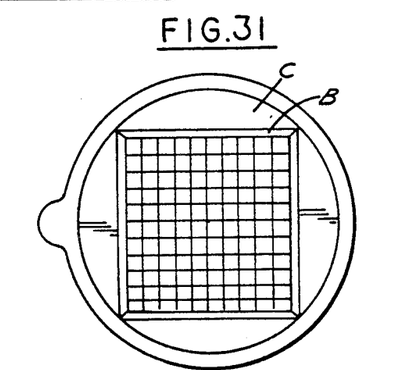
FIG. 31 is a plan view of a further modified form of Rodac package with the insert removed.
Figure 32:
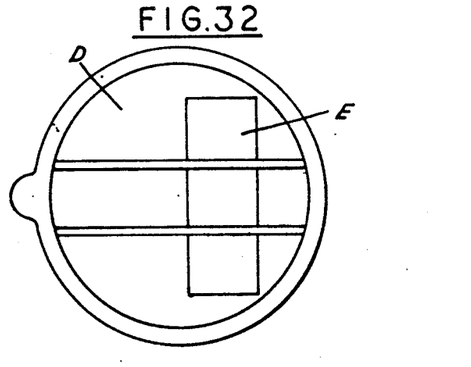
FIG. 32 is a plan view of another modified form of Rodac package.
Figure 33:
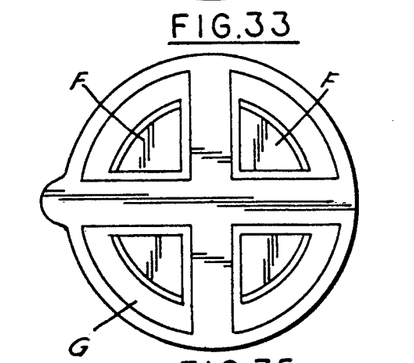
FIG. 33 is a plan view of another modified form of Rodac package.

In the form of Rodac package shown in FIGS. 29 and 30, insert 36d and container 30d have cooperating transverse ribs 80, 81 which divide the media into four isolated areas. Further, the peripheral wall 39d is rectangular such that when the insert 36d is removed, four isolated Rodac areas A are provided. If different media are provided in each of the four isolated areas of the container, the same Rodac device can be utilized for four different tests. If required, small ribs 82 can be provided on the underside of the insert 36d defining grooves in the media in a square pattern to facilitate determination of the extent of growth. In the modified form shown in FIG. 31, the peripheral wall of the insert is rectangular to define a rectangular Rodac area B spaced upwardly from the remainder of the media at area C. In this device, the square form of media can be utilized for Rodac procedure while the area C at the lower level can be utilized for testing as by swabs. In the form shown in FIG. 32, the insert and the container are provided with three interengaging walls like walls 81, 82 which divide three isolated media areas, each of which has a lower area D and a raised rectangular area E. In the form shown in FIG. 33, the media is defined by the insert and container are similarly provided with interengaging walls which divide the media into four isolated media areas, each quadrant including a raised quadrant F surrounded by a lower planar surface G, once again, for purposes of performing both Rodac and conventional procedures.

Each of the forms shown in FIGS. 29–34 comprises a thermoformed plastic insert and a thermoformed plastic container.

Figure 34:
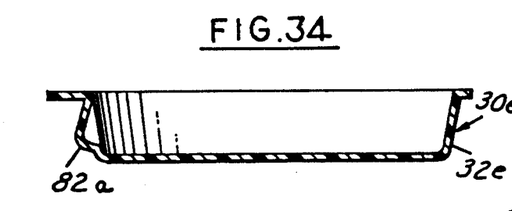
FIG. 34 is a vertical sectional view of another modified form of culture media package.
Figure 35:
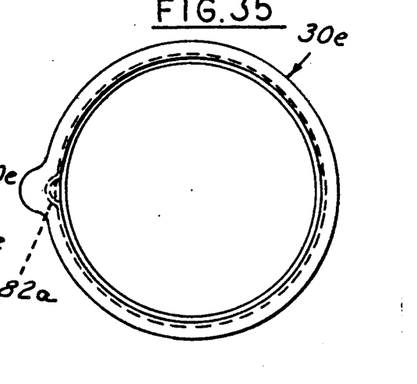
FIG. 35 is a plan view of the culture media package shown in FIG. 34.
Figure 36:
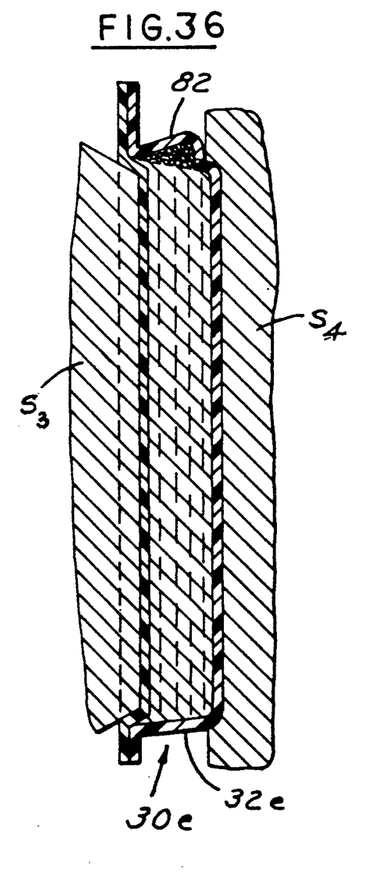
FIG. 36 is a vertical sectional view of the package shown in FIGS. 34 and 35 and positioned for solidification of the culture media.

In the form shown in FIG. 34, the container 30e has the space for gas and bubbles formed by a deformed portion 82a of the peripheral wall 32d. In this form, no groove is needed. When the package is filled and sealed, it may be inverted 90° between cooled members $S_3$, $S_4$ to hold the package until the culture media has solidified.

Figure 27:
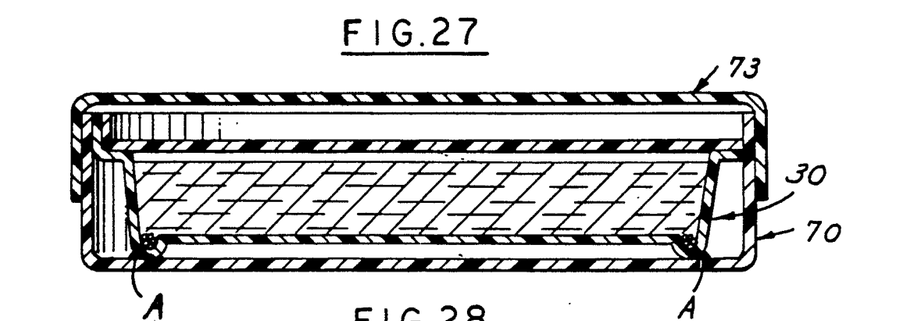
FIG. 27 is a sectional view of a modified form of culture media package.
Figure 28:
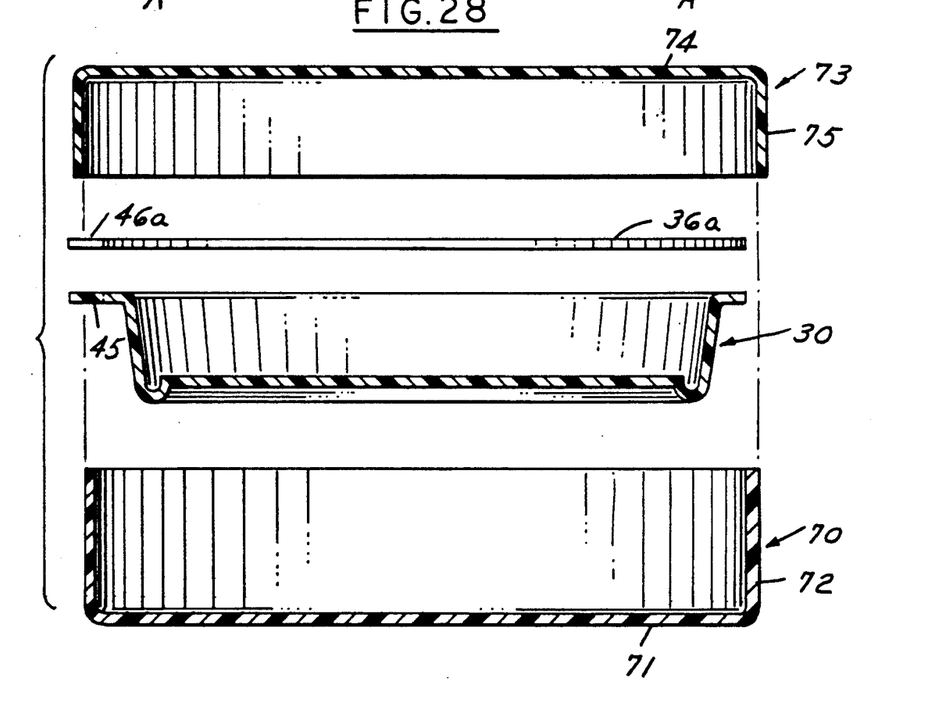
FIG. 28 is an exploded sectional view of the package shown in FIG. 27.

In the form of culture media package shown in FIGS. 27 and 28, the package comprises a standard plastic Petri dish including a bottom member 70 having a flat bottom wall 71 and peripheral cylindrical wall 72. A modified culture package is placed into the bottom member 70. The package includes an insert 36a that is flat and is sealed to the container 30. When the package is placed in the bottom member it is adhered to the top surface of bottom wall 71 by adhesive as at A. The tabs 45, 46a are flexed and functionally engage the peripheral wall 72. A conventional cover 73 having a top wall 74 and peripheral wall is then telescoped over the member 70.

In each form of package, the overall configuration is substantially that used in conventional Petri dishes. Accordingly, they can be handled in a conventional manner to which the users are accustomed.

The container 30 may be made of various plastic materials which should have the following properties: good gas barrier, especially to oxygen. Excellent moisture barrier. The material must also be relatively stiff and have excellent clarity. The material could be a monolithic structure such as PET or PETG or amorphous nylon, or it could be a multi-layered structure with one layer for stiffness (PET, PETG), one layer for barrier (EVA) and one layer for sealability (Surlyn, EVA, polyethylene).

The inserts may be made of various materials which should have the following properties: relatively flexible material, excellent moisture barrier, good gas barrier, especially to oxygen and it must have excellent clarity. It could be a monolithic structure such as PETG, PET, or amorphous nylon, or it could be a multi-layered structure with one layer for stiffness (PET, PETG), one layer for barrier (EVA), and one layer for sealability (Surlyn, EVA, polyethylene).

The cover may be made of various materials having the properties of protecting the package from dirt and contaminants as follows: the material must be relatively stiff and have excellent clarity. Material could consist of PETG, PET or other suitable formable material. Satisfactory materials comprise polystyrene, polyethylene terephthalate (glycol-modified) polyvinyl chloride or other suitable formable polymer. The material should be relatively stiff and have excellent clarity.

The container, insert and cover should preferably be transparent and clear to facilitate viewing the media from the top and bottom.

It can thus be seen that there has been provided a culture media package comprising a container having a bottom wall and a peripheral side wall, a removable insert over the top wall and having a portion projecting into the container to define a planar undersurface bonded to the container and a removable protective cover over said container and insert. The container and insert having radially extending flanges which are heat bonded to one another. The package is made by filling the container with molten culture medium in a sterile environment, sealing the insert to the container in a sterile environment, inverting the sealed container such that the molten medium contacts the planar surface of the insert permitting any gases and bubbles to rise toward the bottom of the container and maintaining the container with the insert there on an inverted position until the culture medium has solidified. The removable cover is thereafter applied to the sealed package of the container and insert. The package is preferably made from continuous molded strips of connected containers and connected inserts which are filled with medium and sealed, severed from one another, thereafter inverted while the culture medium is still molten and permitted to remain in the inverted position until the culture medium has solidified.

What is claimed is:
1. A sterile culture media package comprising
   a container having a bottom wall and a peripheral side wall,
   said container having a peripheral flange extending outwardly from the peripheral side wall,
   a removable insert comprising a bottomwall overlying said container and a peripheral flange extending outwardly from the peripheral side wall and overlying the peripheral flange of said container,
   said package being substantially filled with a culture medium in contact and solidified in situ on the surface of the bottom wall of the insert,
   said container including an integral portion defining a space adjacent the bottom wall into which gases and bubbles present after the package is filled and sealed have migrated,
   said peripheral flange of said container and said peripheral flange of said insert being in contact and sealed to one another to form a sterile package.
2. The culture media package set forth in claim 1 wherein said integral portion defining a space comprises a downwardly extending peripheral groove at the area of juncture of the bottom wall of the container with the peripheral wall of the container.
3. The culture media package set forth in claim 1 wherein said integral portion defining a space comprises an enlarged portion of the side wall of the container.
4. The culture media package set forth in claim 1 wherein said peripheral wall of said container tapers upwardly and outwardly from the base wall, said insert having a peripheral side wall extending axially inwardly toward the bottom wall of the container.

5. The culture media package set forth in claim 1 wherein said insert includes a portion defining a tab for engagement of the insert in order that the insert may be manually removed from its relationship to the container.

6. The culture media package set forth in claim 5 wherein said tab is flexible.

7. The culture media package set forth in claim 1 wherein said peripheral wall of said insert tapers upwardly and outwardly from the bottom wall toward the flange of the insert.

8. The culture media package set forth in claim 7 wherein said peripheral wall of said insert forms a greater angle with the axis of the container then the angle of the peripheral wall of the container makes with a vertical.

9. The culture media package set forth in claim 1 wherein said peripheral wall of said insert extends downwardly from the bottom wall of the insert.

10. The culture media package set forth in claim 9 wherein portions of said bottom wall of said insert are spaced axially from other portions to define different levels on the media.

11. The culture media package set forth in claim 10 wherein said container and insert define spaces, said media in said spaces differing from one another.

12. The culture media package set forth in any of claims 9-11 including a cover having spaced projections engaging the flange of said insert holding said cover in spaced relation to said insert.

13. The culture media package set forth in claim 1 wherein said container has a non-circular configuration in transverse cross section, said flanges of said container and said insert being sealed to one another along a complementary configuration but having portions extending circumferentially in unsealed relationship so that the peripheral edges of the flanges in the unsealed portions combine with the remainder of the configuration of the container and insert to form a circle.

14. The culture media package set forth in claim 13 including a cover having a base wall and a cylindrical peripheral wall telescoped over said flanges of said insert and said container.

15. The culture media package set forth in claim 1 wherein said peripheral flanges having portions in overlying and spaced relation such that portion of the insert can be grasped for removal of the insert.

16. The culture media package set forth in claim 1 wherein said insert comprises a flat sheet.

17. The culture media package set forth in claim 16 including a second container having a base wall and a peripheral wall, said first container package being telescoped in said second container and a cover having a top wall and a side wall telescoped onto said second container.

18. The culture media package set forth in claim 15 including means adhering said first mentioned container in said second container.

19. The culture media package set forth in claim 16 wherein said integral portion defining a space comprises a downwardly extending peripheral groove at the area of juncture of the bottom wall of the container with the peripheral wall of the container, said means for adhering comprises adhesive applied to the exterior of the bottom wall of the first container beneath said groove.

20. The culture media package set forth in any of claims 1-19 including a cover having a base wall and a peripheral flange telescoped over said flanges of said insert and container.

21. The culture media package set forth in claim 20 wherein said base of said cover includes a plurality of circumferentially spaced projections extending toward the insert such that when the insert is removed, said projections engage the flange of said container and maintain the base wall of the cover in spaced relationship to the surface of the media.

22. The culture media package set forth in any of claims 1-21 wherein said container and insert are made of plastic.

23. The method of forming a sterile culture media package comprising forming a container having a bottom wall, a peripheral wall and an integral flange extending outwardly from said peripheral wall, forming an insert having a bottom wall overlying said container and a peripheral flange extending outwardly from said peripheral wall of said insert and overlying the peripheral flange of said container, filling the container with a culture medium to a predetermined level, applying the insert in overlying relationship to the container, moving the insert to bring the flange of the insert into contact with the flange of the container, sealing the flanges throughout the periphery thereof, inverting the sealed container and insert while the medium is molten to bring the culture medium into contact with the surface of the bottom wall of the insert, permitting the culture medium to solidify thereby forming the medium in situ on the under side of the bottom wall of the insert, and thereafter reinverting the resultant package.

24. The method set forth in claim 23 including the step of evacuating and flushing the area between the insert and the medium in the container.

25. The method set forth in claim 23 wherein said step of sealing is by heat bonding.

26. The method set forth in claim 23 wherein said steps are performed in a sterile environment.

27. The method set forth in claim 23 including the step of stacking said packages in a vertical array and enclosing them in a container for handling.

28. The method set forth in claim 23 wherein said step of inverting said sealed container and insert comprises inverting said container at an angle between about 90° to 180°.

29. The method set forth in claim 23 wherein said step of inverting said container comprises inverting said container about 180°.

30. The culture media package set forth in any of claims 23-29 including the step of forming an integral portion in said container defining a space adjacent the bottom wall into which gases and bubbles present after the package is filled and sealed may migrate.

31. The method set forth in any of claims 23-29 including the step of forming an integral portion in said container defining a space adjacent the side wall into which gases and bubbles present after the package is filled and sealed may migrate.

32. The method set forth in any of claims 23-29 including the step of forming said peripheral wall insert such that it extends downwardly from the bottom wall of said insert.

33. The method set forth in any of claims 23-29 including the step of telescoping said first-mentioned container into a second container and adhering said first-mentioned container to said second container.

34. The method set forth in any of claims 23-29 including providing a cover and forming a plurality of spaced projections on said cover such that when the insert in removed, the projections engage the flange of the container and maintain the base wall of the cover in spaced relationship to the surface of the media.

* * * * *